United States Patent [19]

Nakanishi et al.

[11] Patent Number: 4,623,623

[45] Date of Patent: Nov. 18, 1986

[54] PROCESS FOR PRODUCING L-LYSINE BY FERMENTATION

[75] Inventors: Toshihide Nakanishi; Tomoki Azuma; Toshihiko Hirao; Kiyoji Hattori; Minoru Sakurai, all of Hofu, Japan

[73] Assignee: Kyowa Hakko Kogyo Co., Ltd., Tokyo, Japan

[21] Appl. No.: 740,549

[22] Filed: Jun. 3, 1985

Related U.S. Application Data

[63] Continuation of Ser. No. 405,404, Aug. 5, 1982, abandoned.

[30] Foreign Application Priority Data

Nov. 13, 1981 [JP] Japan ................................ 56-182095

[51] Int. Cl.$^4$ ...................... C12P 13/08; C12N 15/00; C12N 1/20
[52] U.S. Cl. ................................. 435/115; 435/172.2; 435/253; 435/840; 435/843; 935/95; 935/96; 935/106; 935/108
[58] Field of Search ............ 435/253, 115, 172, 172.2, 435/840, 843; 935/95, 96, 106, 108

[56] References Cited

U.S. PATENT DOCUMENTS

| | | | |
|---|---|---|---|
| 2,979,439 | 4/1961 | Kinoshita et al. | 435/115 |
| 3,687,810 | 8/1972 | Kurihara et al. | 435/115 |
| 3,707,441 | 12/1972 | Shiio et al. | 435/115 |
| 3,825,472 | 7/1974 | Kubota et al. | 435/115 |
| 3,871,960 | 3/1975 | Kubota et al. | 435/115 |
| 3,905,867 | 9/1975 | Kurimura et al. | 435/115 |
| 3,929,571 | 12/1975 | Kubota et al. | 435/115 |
| 4,066,501 | 11/1978 | Tosaka et al. | 435/115 |
| 4,169,763 | 10/1979 | Nakayama et al. | 435/115 |
| 4,172,764 | 10/1979 | Heslot et al. | 435/172 |
| 4,275,157 | 6/1981 | Tosaka et al. | 435/115 |

FOREIGN PATENT DOCUMENTS 487641 1/1977 Australia.

Primary Examiner—David M. Naff
Attorney, Agent, or Firm—Antonelli, Terry & Wands

[57] ABSTRACT

A process is disclosed for producing L-lysine by culturing a microorganism obtained by protoplast fusion and having an ability to produce L-lysine in a nutrient medium, forming and accumulating L-lysine in the resulting culture liquor, and recovering the L-lysine therefrom. Also, there are disclosed a number of microorganisms for producing L-lysine which are obtained by protoplast fusion.

3 Claims, No Drawings

PROCESS FOR PRODUCING L-LYSINE BY FERMENTATION

This is a continuation of application Ser. No. 405,404, filed Aug. 5, 1982, now abandoned.

This invention relates to novel microorganisms having an ability to produce L-lysine, and a process for producing L-lysine by fermentation using these microorganisms. More particularly, the present invention relates to microorganisms belonging to the genus Corynebacterium or Brevibacterium and having both an ability to accumulate L-lysine in a considerable amount and a resistance to antibiotics of two or above; microorganisms obtained by the technology of protoplast fusion between parent strains belonging to the same or different genus of Corynebacterium or Brevibacterium and having an ability to accumulate L-lysine in a considerable amount; or microorganisms obtained by protoplast fusion and having both an ability to accumulate L-lysine in a considerable amount and a resistance to antibiotics of two or above. This invention also relates to a process for producing L-lysine by fermentation which comprises culturing the microorganisms in a nutrient medium, accumulating a considerable amount of L-lysine in the resulting culture liquor, and recovering the L-lysine therefrom.

An object of the present invention is to provide a process for producing L-lysine which has a great demand as animal feed, additive to animal feed or food, starting material of a medicament, etc., at an industrially low cost.

Heretofore, as processes for producing L-lysine by fermentation, there have been known processes of using strains having a nutritional requirement for various compounds, strains having sensitivity to various chemicals, or various chemicals-resistant strains, belonging to the genus Corynebacterium, Brevibacterium, Arthrobacter, Pseudomonas, Bacillus, Nocardia, Saccharomyces, Escherichia, Klebsiella, Streptomyces, Alkaligenes, Microbacterium, Acromobacter, and Serratia, and processes of using mutants having a combination of the properties of the abovedescribed microorganisms.

As a result of various studies for obtaining strains having an increased L-lysine productivity, the present inventors have found that a strain capable of producing L-lysine belonging to the genus Corynebacterium or Brevibacterium endowed with a resistance to antibiotics of two or above has a remarkably improved ability to produce L-lysine.

In addition, it has been found that a strain capable of producing L-lysine in high yield can be obtained by utilizing the technology of cell fusion using protoplast to obtain recombinant strain. The process of the present invention enables one to effectively obtain double mutants capable of producing L-lysine in high yield, and is an effective process which enables one to obtain mutants possessing merits of well selected parent strains. It has been found by the present inventors that, in production of L-lysine by fermentation, L-lysine productivity can be remarkably increased by using a mutant having a resistance to antibiotics of two or above, or a strain obtained by protoplast fusion.

The present invention will be described in more detail below.

As the microorganisms of the present invention, there are illustrated L-lysine-producing strains obtained by protoplast fusion between parent strains having different properties, and L-lysine-producing strains obtained by the technology of protoplast fusion or by conventional mutation inducing treatment or spontaneous mutation having a resistance to antibiotics of two or above.

As the strain of the present invention having both an ability to produce L-lysine and a resistance to antibiotics of two or above, there may be used a strain capable of producing L-lysine belonging to the genus Corynebacterium or Brevibacterium which is endowed with a resistance to antibiotics of two or above, or a strain having a resistance to antibiotics of two or above and belonging to the genus Corynebacterium or Brevibaceterium which is endowed with an ability of producing L-lysine. As the strain belonging to the genus Corynebacterium or Brevibacterium and having an ability to produce L-lysine, for example, strains capable of producing L-lysine having a requirement for various nutrients (for example, homoserine, methionine, threonine, histidine, proline, alanine, leucine, isoleucine, valine, serine glutamic acid, pantothenic acid, nicotinic acid amide, acetic acid, adenine, hypoxanthine, inositol, and their combinations), a resistance to various amino acid analogs (for example, analogs of lysine, threonine, methionine, leucine, isoleucine, valine, aspartic acid, tryptophane or histidine, and their combinations), a resistance to nucleic acid analogs, and a resistance to other chemicals (for example, sulfa drugs, penicillin type antibiotics, various organic acids, quinone compounds, quinoline compounds, and their combinations) may be mentiioned. It is also possible to obtain a strain having a resistance to antibiotics of two or above by subjecting the above-mentioned L-lysine-producing strains to mutation. In addition, an L-lysine-producing strain obtained by endowing with the above-described requirement for nurients and a resistance to amino acid analogs, nucleic acid analogs or other chemicals, a strain belonging to the genus Corynebacterium or Brevibacterium and having a resistance of antibiotics of two or above, can also be used in the present invention. Further, the strain to be used in the present invention may have any other property of contributing to L-lysine productivity than the properties mentioned above. As a resistance to antibiotics of two or above, a resistance to two or more of penicillins, cephalosporins, streptomycin, dihydrostreptomycin, rifampicin, chloramphenicol, tetracyclines, spiramycin, erythromycin, kanamycin, kasugamycin, mitomycin C, actinomycin D, polymyxin, colistin, lincomycin, gentamicin, sagamicin, fortimicin, oleandomycin, etc., is mentioned.

Parent strains to be used for obtaining mutants useful in the present invention are microorganisms belonging to the genus Corynebacterium or Brevibacterium known as a glutamic acid-producing strain, such as *Corynebacterium glutamicum* ATCC 13032, *Corynebacterium acetoacidophilum* ATCC 13870, *Brevibacterium lactofermentum* ATCC 13869, *Brevibacterium flavum* ATCC 14067, etc.

Of the microorganisms to be used in the present invention, specific examples of a strain having a resistance to antibiotics of two or above are *Corynebacterium glutamicum* H-3127 (hereinafter referred to as H-3127) (FERM BP-153) and *Brevibacterium lactofermentum* H-3125 (hereinafter referred to as H-3125) (FERM BP-151). Specific examples of a strain having an ability to produce L-lysine obtained by the technology of protoplast fusion are a protoplast fusion strain H-3057 (hereinafter referred to as H-3057) (FERM BP-148) between *corynebacterium glutamicum* H-3122 (hereinafter referred to as H-3122) (FERM BP-150) and *Brevibacterium lactofermentum* H-3126 (hereinafter referred to as H-3126) (FERM BP-152), and a protoplast fusion strain H-3055 (hereinafter referred to as H-3055) (FERM BP-147) between H-3122 and *Corynebacterium glutamicum* H-3119 (hereinafter referred to as H-3119) (FERM BP-149).

Further, there is mentioned a 6-azauracil-resistant strain H-3149 (hereinafter referred to as H-3149) (FERM BP-158) derived from H-3055. In view of deposit with Fermentation Research Institute Agency of Industrial Science and Technology, protoplast fusion strains H-3057, H-3055 and H-3149 are, respectively, designated as *Corynebacterium glutamicum* H-3057 (FERM BP-148), *Corynebacterium glutamicum* H-3055 (FERM BP-147), and *Corynebacterium glutamicum* H-3149 (FERM BP-158) in the Receipt for Application for Deposit of Microorganism, for convenience.

An example of obtaining a protoplast fusion strain of the present invention is described below.

Protoplasts are formed from culture cells as follows. A strain is inoculated in a nutrient medium NB containing 20 g of bouillon powder and 5 g of yeast extract in 1 l of pure water and adjusted to pH 7.2, and cultured with shaking. Absorbance (OD) at 660 nm is measured by means of a turbidimeter and, in the initial stage (OD=0.1 to 0.2) of logarithmic growth phase, penicillin G is added to the culture liquor to make a final concentration of 0.1 to 0.8 μg/ml. Culturing is further continued and, when OD reaches 0.3 to 0.5, cells are collected and washed with SSM medium (containing 10 g of glucose, 4 g of $NH_4Cl$, 2 g of urea, 1 g of yeast extract, 1 g of $KH_2PO_4$, 3 g of $K_2HPO_4$, 0.4 g of $MgCl_2.6H_2O$, 10 mg of $FeSO_4.7H_2O$, 0.2 mg of $MnSO_4.4-6H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin and 1 mg of thiamine hydrochloride in 1 l of pure water and adjusted to pH 7.2; in culturing an amino acid-requiring strain, 50 μg/ml of a required amino acid is further added SSM medium). Then, the cells are again suspended in PFM medium (containing 0.4M sucrose and 0.01M $MgCl_2.6H_2O$ in a 2-fold diluted SSM solution and adjusted to pH 7.0 to 8.5). Lysozyme (0.2 to 2 mg/ml) is added to this cell suspension to keep at 30° to 37° C. for 16 hours. Formation of protoplast is confirmed under an optical microscope. The thus prepared protoplasts of two strains to be fused are counted under an optical microscope and the suspensions are mixed in a protoplast ratio of 1:1. The protoplasts are separated from the mixture by centrifugation and after washing the separated protoplasts with PFM medium, the protoplasts are again suspended in 0.1 ml of PFM medium.

To the suspension is added 2.5 ml of PFM medium containing 40% polyethylene glycol (PEG) 4000, and slowly stirred for 5 minutes.

In the case where a streptomycin-resistant strain and a rifampicin-resistant strain are used, 0.3 ml of the suspension is smeared on RCG agar plate containing 100 μg/ml of streptomycin and 0.05 μg/ml of rifampicin (containing 5 g of glucose, 5 g of casamino acid, 2.5 g of yeast extract, 3.5 g of $K_2HPO_4$, 1.5 g of $KH_2PO_4$, 0.41 g of $MgCl_2.6HCl$, 10 mg of $FeSO_4.7H_2O$, 2 mg of $MnSO_4.4-6H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin, 2 mg of thiamine hydrochloride, 135 g of sodium succinate and 14 g of agar in 1 l of pure water, and adjusted to pH 7.4). After culturing at 30° C. for 12 days, colonies of a strain having a resistance to both streptomycin and rifampicin are obtained.

Any of synthetic medium and natural medium may be used as the medium for the present invention, so long as it properly contains a carbon source, inorganic materials and other necessary nutrients which are assimilable by the strain utilized.

As the carbon source, various carbohydrates, such as glucose, fructose, sorbitol, glycerol, sucrose, starch, starch hydrolyzate, molasses, fruit juice, etc., organic acids, such as acetic acid, fumaric acid, lactic acid, etc., and alcohols, such as ethanol, methanol, etc., may be used.

As the nitrogen source, ammonia, inorganic and organic ammonium salts, such as ammonium chloride, ammonium sulfate, ammonium acetate, ammonium phosphate, etc., urea, amines, other nitrogen-containing compounds and peptone, meat extract, yeast extract, corn steep liquor, casein hydrolyzate, soybean meal acid hydrolyzate, various microbial cells, digest of microbial cells, etc., may be used.

As the inorganic materials, potassium dihydrogen phosphate, dipotassium hydrogen phosphate, magnesium phosphate, magnesium sulfate, sodium chloride, ferrous sulfate, manganese sulfate, copper sulfate, calcium carbonate, etc., are used. When a microorganism to be used in the present invention requires specific nutrients for growth, an appropriate amount of the nutrients are added to the medium. In some cases, these nutrients are added as components of the natural substances exemplified as the nitrogen source.

Further, the productivity of L-lysine by the present microorganism can be, in some cases, enhanced by adding other various additives, for example, various antibiotics, α-aminobutyric acid, cysteine, leucine, leucine fermentation liquor, aspartic acid, glutamic acid, etc., to the medium.

Culturing is carried out under aerobic conditions, for example, by shaking culture, agitation submerged culture, etc. The temperature for culturing is generally 20°–40° C., and the pH of the medium is in a range of 3 to 9, and is preferably maintained at around neutral, but culturing can be carried out under conditions which are out of this range so long as the microorganism used can grow. The pH of the medium is adjusted with calcium carbonate, acid or alkali solution, ammonia, pH buffering agent, etc. Usually, after culturing for 1 to 6 days, L-lysine is formed and accumulated in the resulting culture liquor.

After the completion of culturing, precipitates, such as cells, are removed from the culture liquor and L-lysine can be recovered from the culture liquor by use of the conventional methods, such as ion-exchange resin treatment, concentration, adsorption, salting-out in combination.

Practice of specific embodiments of the invention is illustrated by the following representative examples.

EXAMPLE 1

(Preparation of H-3127 and H-3125)

*Corynebacterium glutamicum* FERM P-3634 (NRRL-B-8183) (hereinafter referred to as P-3634) (having a requirement for homoserine and leucine and a resistance to thialysine and sulfamethazine) having been in advance cultured overnight in a bouillon medium is directly smeared on a bouillon agar plate medium containing 200 μg/ml of dihydrostreptomycin. After maintaining the medium at 30° C. for 2 to 10 days, a spontaneous mutant strain is selected from the colonies growing, and the mutant cells are suspended in a 0.1N trismaleate buffer solution (pH 6.0) in a concentration of $10^8$ cells/ml. To the suspension is added N-methyl-N'-nitro-N-nitrosoguanidine to make a final concentration of 0.2 mg/ml. After allowing the suspension to stand for 30 minutes at room temperature, the suspension is smeared on a bouillon agar plate medium containing 1 unit/ml of penicillin G. H-3127 is obtained as the mutants selected in the colonies growing. H-3127 is clearly discriminated from the parent strain P-3634 in that the former possesses a resistance to both dihydrostreptomycin and penicillin G as shown in Table 1. Also, a dihydrostreptomycin-resistant strain obtained from *Brevibacterium lactofermentum* H-3056 (FERM BP-154) (hereinafter referred to as H-3056) having an ability to produce lysine (having a resistance to thialysine and a requirement for leucine and partial requirement for homoserine) is subjected to the same spontaneous mutation as described above. H-3125 is obtained as a mutant strain selected in the colonies growing on a bouillon agar plate medium containing 50 μg/ml of rifampicin. H-3125 is clearly discriminated from the parent strain (H-3056) in that the former has a resistance to both dihydrostreptomycin and rifampicin as shown in Table 1.

TABLE 1

|  |  | P-3634 | H-3127 | H-3056 | H-3125 |
|---|---|---|---|---|---|
| Penicillin G | 0.5 μg/ml | − | ++ | − | − |
|  | 1.0 μg/ml | − | + | − | − |
| Dihydro-streptomycin | 100 μg/ml | − | ++ | − | ++ |
|  | 200 μg/ml | − | ++ | − | ++ |
| Rifampicin | 25 μg/ml | − | − | − | ++ |
|  | 50 μg/ml | − | − | − | ++ |
| Nothing added |  | ++ | ++ | ++ | ++ |

(++: sufficient growth; +: growth to some extent; −: no growth)

EXAMPLE 2

(Preparation of H-3057)

H-3122 having an ability to produce L-lysine (having a requirement for leucine and partial requirement for homoserine and a resistance to thialysine, sulfamethazine and rifampicin) derived from P-3634 and H-3126 (having a resistance to thialysine and streptomycin) derived from *Brevibacterium lactofermentum* FERM P-1837 (ATCC 21888) having an ability to produce L-leucine are prepared, and protoplast fusion is conducted in the same manner as described hereinbefore to obtain a number of fusion strains having a resistance to both rifampicin and streptomycin. With respect to the parent strains H-3122 and H-3126, the appearance frequency of the spontaneous mutant strains having a resistance to both rifampicin and streptomycin are $1.3 \times 10^{-8}$ and $6.5 \times 10^{-9}$, respectively; whereas that by the technology of protoplast fusion is $1.1 \times 10^{-7}$. Accordingly, protoplast fusion endows the parent strains with the double resistance at least 10 times as much as spontaneous mutation. Thus, it is confirmed that strains having a resistance to both rifampicin and streptomycin appear with high frequency by the technology of the protoplast fusion.

Various properties of H-3057, selected as a typical example of the protoplast fusion strain, are shown in Table 2 in comparison with those of parent strains. As is clear from the table, H-3057 has the same properties as H-3126 with respect to sensitivity to sulfamethazine and resistance to streptomycin, and has the same properties as H-3122 with respect to a requirement for leucine, sensitivity to 2-thiazolealanine, resistance to rifampicin, ability to reduce NO₃, and productivity of L-lysine. Such strain cannot be obtained as a result of spontaneous mutation by single treatment, and hence H-3057 is a typical fusion-produced strain.

TABLE 2

|  | S—Lys | Sulfa-metha-zine | 2TA | Leu | STM | RIF | NO₃ Reduction | Productivity |
|---|---|---|---|---|---|---|---|---|
| H-3122 | R | R | S | necessary | S | R | ++ | L-Lys |
| H-3126 | R | S | R | unnecessary | R | S | ± | L-Leu |
| H-3057 | R | S | S | necessary | R | R | ++− | L-Lys |

R: Resistant;
S: Sensitive;
S—Lys: S—(2-aminomethyl)-cysteine; (Thialysine)
2TA: 2-thiazolealanine;
Leu: leucine;
STM: streptomycin;
RIP: rifampicin.

EXAMPLE 3

(Preparation of H-3055)

H-3122 and H-3119 (having partial requirement for homoserine, no requirement for leucine and a resistance to thialysine, 2-thiazolealanine, α-amino-β-hydroxybutyric acid and streptomycin) derived from *Corynebacterium glutamicum* ATCC 21543 are subjected to the protoplast fusion treatment as described hereinbefore to obtain a strain having a resistance to both streptomycin and rifampicin. L-lysine productivity and various properties of this strain are examined. Appearance frequency of strains acquiring resistance to both streptomycin and rifampicin as a result of spontaneous mutation from H-3122 and H-3119 are $1.0 \times 10^{-8}$ and $2.0 \times 10^{-8}$, respectively. On the other hand, by the above-described protoplast fusion, appearance frequency of strains acquiring the double resistance is $4 \times 10^{-7}$, which is about 20 to 40 times as high as that by mutation. Thus, it is confirmed that strains having a resistance to both rifampicin and streptomycin appear with high frequency by the protoplast fusion. As a strain having a remarkably improved L-lysine productivity, there is illustrated, for example, H-3055. Various properties of this strain are shown in Table 3 in comparison with those of parent strains.

H-3055 has the same non-requirement for leucine and the same sensitivity to sulfamethazine and streptomycin as H-3119, and has the same sensitivity to 2-thiazolealanine and the same resistance to rifampicin as H-3122. With respect to growth, and productivity of L-lysine, H-3055 is more improved than the parent strains.

TABLE 3

|  | S—Lys | Leu | Sulfa-methazine | 2TA | STM | RIF | Growth w/o Leu | Growth with Leu | Productivity of Lys HCl * |
|---|---|---|---|---|---|---|---|---|---|
| H-3122 | R | necessary | R | S | S | R | − | ++ | 36% |
| H-3119 | R | unnecessary | S | R | R | S | + | + | 25% |
| H-3055 | R | unnecessary | S | S | R | R | ++ | +++ | 38% |

R: Resistant;
S: Sensitive;
*Yield based on sugar (under optimal conditions) (0.5 g/l of L-Leu is added for H-3122)

EXAMPLE 4

(Preparation of H-3149)

Cells of H-3055 are suspended in a 0.1N trismaleate buffer solution (pH 6.0) in a concentration of $10^8$ cells/ml. To the suspension is added N-methyl-N'-nitro-N-nitrosoguanidine to make a final concentration of 0.2 mg/ml. After allowing the suspension to stand for 30 minutes at room temperature, the suspension is smeared on a bouillon agar plate medium containing 1 mg/ml of 6-azauracil. After maintaining the medium at 30° C. for 2 to 10 days, H-3149 is obtained as a mutant strain selected in the colonies growing. Table 4 shows how sensitive H-3055 and H-3149 are to 6-azauracil.

TABLE 4

|  |  | H-3055 | H-3149 |
|---|---|---|---|
| Nothing added |  | ++ | ++ |
| 6-Azauracil | 0.5 mg/ml | − | ++ |
|  | 1 mg/ml | − | + |
|  | 3 mg/ml | − | − |

EXAMPLE 5

H-3057 is used as a seed strain.

The strain is inoculated in a 300 ml-Erlenmeyer flask containing 20 ml of a seed medium (pH 7.2) comprising 40 g/l of glucose, 3 g/l of urea, 1.5 g/l of $KH_2PO_4$, 0.5 g/l of $K_2HPO_4$, 0.5 g/l of $MgSO_4.7H_2O$, 50 µg/l of biotin, 20 g/l of peptone and 5 g/l of yeast extract, and cultured at 30° C. for 24 hours. Then, 2 ml of the seed culture is put into a 300 ml-Erlenmeyer flask containing 20 ml of a fermentation medium (pH 7.2) comprising 100 g/l of blackstrap molasses (as glucose), 20 g/l of soybean meal acid hydrolyzate (as soybean meal), 5 g/l of ammonium sulfate, 1 g/l of L-leucine, 3 g/l of urea, 0.5 g/l of $MgSO_4.7H_2O$, 0.7 g/l of $KH_2PO_4$ and 30 g/l of $CaCO_3$, and cultured with shaking (220 rpm) at 30° C. for 3 days. As a result, 39.5 g/l of L-lysine (as monohydrochloride, which will be hereinafter applied) is formed and accumulated in the culture liquor. Amounts of L-lysine, in case where parent strains H-3122 and H-3126 are cultured at the same time under the same conditions as a control, are 36 g/l and 0.5 g/l, respectively.

After a completion of culturing, 1 l of the culture liquor of the present strain is centrifuged, and the resulting supernatant is passed through a column of Diaion SK-1B (H+ form, trade mark of strongly acidic ion-exchange resin made by Mitsubishi Chemical Industries, Ltd.) to adsorb thereon L-lysine. After washing the column with water, L-lysine is eluted with a dilute aqueous ammonia to collect and concentrate L-lysine-containing fractions. The pH of the concentrate is adjusted to pH 2 with hydrochloric acid, and cooled while adding thereto ethanol to thereby form crystals of L-lysine. Thus, 31 g of crystals of L-lysine is obtained.

EXAMPLE 6

H-3055 is used as a seed strain

The strain is inoculated in the same seed medium as used in Example 5, and cultured at 30° C. for 24 hours. Then, 2 ml of the seed culture is put into a 300 ml-Erlenmeyer flask containing 20 ml of a fermentation medium (pH 7.2) comprising 100 g/l of blackstrap molasses (as glucose), 40 g/l of ammonium sulfate, 0.5 g/l of $KH_2PO_4$, 0.5 g/l of $MgSO_4$ and 30 g/l of $CaCO_3$, and cultured with shaking (220 rpm) at 32° C. for 3 days. As a result, 41 g/l of L-lysine is accumulated in the culture liquor. Amounts of L-lysine, in case where parent strains H-3122 and H-3119 are cultured at the same time under the same conditions as a control, are 2.5 g/l and 24 g/l, respectively. L-lysine productivity of H-3122 is seriously low because the culture medium does not contain L-leucine which the strain requires.

EXAMPLE 7

H-3127 and H-3125 are used as seed strains. Each of the strains is inoculated in the same seed medium as used in Example 5, and cultured at 30° C. for 24 hours. Then, 2 ml of each seed culture is inoculated in the same fermentation medium as used in Example 5, and cultured with shaking (220 rpm) at 30° C. for 3 days. As a result, L-lysine is accumulated in the culture liquor in amounts given in Table 5. Amounts of L-lysine, in case where parent strains P-3634 and H-3056 are cultured at the same time under the same conditions as a control, are also shown in Table 5.

TABLE 5

|  | Amount of L-lysine (g/l) |
|---|---|
| P-3634 | 36 |
| H-3127 | 39 |
| H-3056 | 31 |
| H-3125 | 36 |

EXAMPLE 8

H-3055, H-3127, H-3125 and H-3057 are used as seed strains. Each of the strains is inoculated in the same seed culture as used in Example 5, and cultured at 30° C. for 24 hours. Then, 2 ml of each seed culture is put into a 300 ml-Erlenmeyer flask containing 20 ml of a fermentation medium (pH 7.2) comprising 100 g/l of glucose, 20 g/l of ammonium chloride, 20 g/l of corn steep liquor, 200 μg/l of biotin, 1 g/l of KH$_2$PO$_4$, 0.5 g/l of MgSO$_4$.7H$_2$O, 0.2 mg/ml of thiamine hydrochloride, 10 mg/l of FeSO$_4$.7H$_2$O, 10 mg/l of MnSO$_4$.4H$_2$O, 3 g/l of urea and 20 g/l of CaCO$_3$, and cultured with shaking (220 rpm) at 30° C. for 3 days. Amounts of L-lysine thus accumulated are shown in Table 6 together with amounts of L-lysine accumulated in culturing parent strains P-3634, H-3122, H-3126 and H-3119 at the same time under the same conditions as a control. Additionally, with L-leucine-requiring strains, 0.5 g/l of L-leucine is added to the medium.

TABLE 6

|       | Amount of L-lysine (g/l) |
|-------|--------------------------|
| H-3125 | 36.5 |
| H-3127 | 40.0 |
| H-3055 | 41.0 |
| H-3057 | 39.0 |
| P-3634 | 36.5 |
| H-3122 | 37.0 |
| H-3119 | 29.0 |
| H-3126 | 0.5 |

EXAMPLE 9

H-3055 is used as a seed strain. The strain is inoculated in a 300 ml-Erlenmeyer flask containing 30 ml of the same seed medium as used in Example 5, and cultured with shaking (220 L rpm) at 30° C. for 24 hours. Then, 100 ml of the seed culture is put into a 2 l-jar fermenter containing 0.8 l of a fermentation medium comprising 30 g/l of glucose, 3 g/l of ammonium acetate, 1 g/l of KH$_2$PO$_4$, 0.5 g/l of MgSO$_4$.7H$_2$O, 10 mg/l of FeSO$_4$.7H$_2$O, 10 mg/l of MnSO$_4$, 200 μg/l of biotin, 200 μg/l of thiamine hydrochloride and 2 g/l of soybean meal acid hydrolyzate (as soybean meal), and cultured at an aeration rate of 1 l/min., a stirring speed of 800 rpm and at 35° C. for 55 hours while adjusting pH of the fermentation liquor to 6.8 with a mixture of acetic acid and ammonium acetate (mixing ratio of acetic acid-:ammonium acetate=6:1; concentration of acetic acid in the mixture solution: 60%). As a result, 39 g/l of L-lysine is accumulated in the culture liquor. Amounts of L-lysine, in case where parent strains H-3122 and H-3119 are cultured at the same time under the same conditions as a control, are 35 g/l and 27 g/l, respectively.

EXAMPLE 10

H-3149 is used as a seed strain

The strain is inoculated in the same seed medium as used in Example 5, and cultured at 30° C. for 24 hours. Then, 2 ml of the seed culture is inoculated in a 300 ml-Erlenmeyer flask containing 20 ml of a fermentation medium (pH 7.2) comprising 100 g/l of blackstrap molasses (as glucose), 40 g/l of ammonium sulfate, 0.5 g/l of KH$_2$PO$_4$, 0.5 g/l of MgSO$_4$ and 30 g/l of CaCO$_3$, and cultured at 32° C. for 3 days under shaking (220 rpm). As a result, 43 g/l of L-lysine is accumulated in the culture liquor. The amount of L-lysine, in case where parent strain H-3055 is cultured at the same time under the same condition as a control, is 41 g/l.

What is claimed is:

1. A process for producing L-lysine, which comprises culturing a protoplast fusion strain H-3057 (FERM BP-148) obtained by protoplast fusion between *Corynebacterium glutamicum* H-3122 (FERM BP-150) and *Brevibacterium lactofermentum* H-3126 (FERM BP-152), a protoplast fusion strain H-3055 (FERM BP-147) obtained by protoplast fusion between *Corynebacterium glutamicum* H-3122 (FERM BP-150) and *Corynebacterium glutamicum* H-3119 (FERM BP-149), or *Corynebacterium glutamicum* H-3149 (FERM BP-158) in a nutrient medium, forming and accumulating L-lysine in the resulting culture liquor, and recovering the L-lysine therefrom.

2. The process according to claim 1, wherein said culturing is conducted at 20° to 40° C. for 1 to 6 days.

3. A biologically pure culture of a protoplast fusion strain H-3057 (FERM BP-148) having a resistance to streptomycin and rifampicin obtained by protoplast fusion between *Corynebacterium glutamicum* H-3122 (FERM BP-150) and *Brevibacterium lactofermentum* H-3126 (FERM BP-152), a protoplast fusion strain H-3055 (FERM BP-147) having a resistance to streptomycin and rifampicin obtained by protoplast fusion between *Corynebacterium glutamicum* H-3122 (FERM BP-150) and *Corynebacterium glutamicum* H-3119 (FERM BP-149), or a microorganism strain H-3149 (FERM BP-158) having a resistance to streptomycin, rifampicin and 6-azauracil derived from the protoplast fusion strain H-3055, which culture possesses the ability to produce L-lysine.

* * * * *